United States Patent [19]

Costello et al.

[11] Patent Number: 5,043,467

[45] Date of Patent: Aug. 27, 1991

[54] CHEMICAL PROCESS

[75] Inventors: Alan Costello, Ashton Under Lyne; John D. Jones, Bury, both of England

[73] Assignee: Imperial Chemical Industries PLC, London, England

[21] Appl. No.: 489,780

[22] Filed: Mar. 5, 1990

Related U.S. Application Data

[63] Continuation of Ser. No. 85,730, Aug. 17, 1987, abandoned.

[30] Foreign Application Priority Data

Sep. 10, 1986 [GB] United Kingdom ................ 8621791
Mar. 27, 1987 [GB] United Kingdom ................ 8707347

[51] Int. Cl.$^5$ .......................................... C07C 121/66
[52] U.S. Cl. .................................................... 558/392
[58] Field of Search .......................................... 558/392

[56] References Cited

U.S. PATENT DOCUMENTS

| | | | |
|---|---|---|---|
| 4,447,446 | 5/1984 | Kay et al. | 558/392 |
| 4,575,557 | 3/1986 | Jones et al. | 549/366 |
| 4,579,581 | 4/1986 | Kay et al. | 558/392 |
| 4,663,481 | 5/1987 | Jones et al. | 564/124 |
| 4,786,747 | 11/1988 | Jones et al. | 558/392 |

Primary Examiner—Prince E. Willis
Assistant Examiner—Jerry D. Johnson
Attorney, Agent, or Firm—Cushman, Darby & Cushman

[57] ABSTRACT

A process for the production of a substituted amide of the formula:

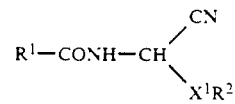

where $R^1$ is an optionally substituted aryl group, $X^1$ is —O— or —S— and $R^2$ is an optionally substituted alkyl, alkenyl, or alkynyl group or $X^1R^2$ is an N-linked 5-membered nitrogen heterocycle comprising the halogenation, preferably bromination, in an inert solvent of a N-cyanomethyl-amide of the formula $R^1$—CONH.CH$_2$CN, followed by addition to the halogenated mixture, or to the mixture as halogenation is taking place, of a heterocyclic tertiary amine in a proportion of from about 1.0 to about 2.5 moles, and preferably from 1.3 to 2.1 moles, for each mole of halogen reacted, and finally treatment of the resulting quaternary salt with an alcohol, thiol or amine of the formula $R^2X^1H$.

7 Claims, No Drawings

CHEMICAL PROCESS

This is a continuation of application Ser. No. 085,730, filed Aug. 17, 1987, which was abandoned.

This invention relates to a process for the preparation of certain substituted amide derivatives which are useful by virtue of their herbicidal and fungicidal properties.

Substituted amide derivatives of the formula (I):

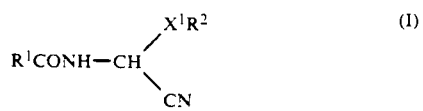

in which $R^1$ is an aryl group, $X^1$ is —O— or —S— and $R^2$ is an optionally substituted alkyl, alkenyl or alkynyl group, or $X^1R^2$ is an N-linked 5-membered nitrogen heterocycle such as pyrazole or 1,2,4-triazole which are proposed for use as herbicides and fungicides, are described in our European Patent Specification No. 0059536, together with processes for their preparation. One such process involves a sequence of chemical reactions in the following scheme:

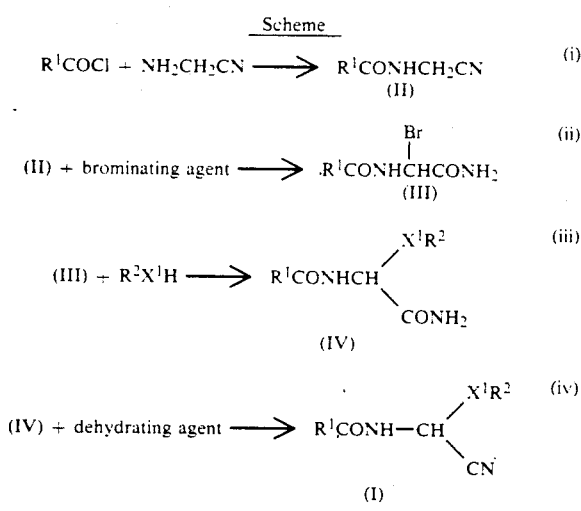

In step (i) of the Scheme, an acid chloride $R^1COCl$ is reacted with aminoacetonitrile by a conventional procedure to obtain the compound (II). This is then treated in step (ii) with a solution of bromine in glacial acetic acid to give the brominated derivative (III). The bromination simultaneously hydrates the cyano group to a carbamoyl group —$CONH_2$, necessitating treatment with a dehydrating agent later. In step (iii), the bromo compound (III) is reacted with an appropriate alcohol or thiol, or 5-membered nitrogen heterocycle to obtain the carbamoyl compound (IV) which is then treated with the dehydrating agent in step (iv) to convert it to the corresponding cyano compound (I).

This sequence of reactions suffers from the disadvantages not only of requiring the final dehydration step to restore the cyano group but also of the fact that the bromination of the compound (II) in glacial acetic acid gives rise to a highly corrosive reaction medium consisting of a mixture of acetic acid, acetyl bromide and hydrogen bromide. Furthermore, the yields obtained of the bromoamide (III) tend to be somewhat inconsistent. Some improvement in yields may be achieved, as described in our European Specification No. 0144177, by the reverse procedure in step (ii) of adding the compound (II), dissolved in glacial acetic acid, to bromine, but the other disadvantages remain.

Attempts have therefore been made to effect the bromination step so that the cyano group is preserved intact and the production of undesirable by-products is avoided. In our British Patent Specification No 2146983 we have described an alternative reaction scheme in which the bromination step (ii) is carried out in an inert solvent, in particular in ethyl acetate. This is, however, successful in avoiding hydration of the cyano group only so long as the bromination takes place in dilute solution, and it is also necessary to add rapidly the bromine in step (ii) and the reactant $R^2X^1H$ (e.g. an alcohol) in step (iii). These features render the procedure inconvenient for large-scale production and it is also found that, under these conditions, the yields of the final product (I) are unpredictable.

We have now found a method of synthesising the amide derivatives (I) which retains the advantage of avoiding hydration of the cyano group in the starting material but which avoids the difficulties inherent in the procedure last mentioned; thus lending itself to satisfactory large scale production.

According to the present invention we provide a process for the production of a substituted amide derivative of the formula (I):

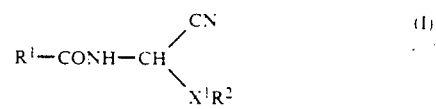

in which $R^1$ is an optionally substituted aryl radical, $X^1$ is —O— or —S— and $R^2$ is an optionally substituted alkyl, alkenyl or alkynyl group or $X^1R^2$ is an N-linked 5-membered nitrogen heterocycle such as pyrazole or 1,2,4-triazole, the process comprising the steps of (a) treatment with a halogenating agent in an inert solvent of an N-cyanomethylamide of the formula (II):

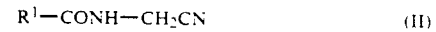

(b) addition to the halogenation mixture, during or after halogenation, of a heterocyclic tertiary amine in the proportion of about from 1.0 to about 2.5 moles of the amine for each mole of halogenating agent reacted, resulting in the formation of a quaternary salt of the formula (V):

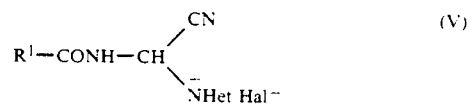

where Hal represents a halogen atom and Het represents the heterocyclic residue, and (c) treating the salt (V) with a reagent of the formula $R^2X^1H$.

In the above-mentioned compounds of formulae (I), (II) and (V), the optionally substituted aryl group $R^1$ may be a phenyl or naphthyl radical. Examples of substituents which may be present include fluorine, chlorine, bromine, iodine, $C_1$-$C_4$ alkoxy, methylenedioxy and ethylenedioxy, $C_{1-4}$ alkyl, $C_{1-4}$ alkylthio, $C_{1-4}$ haloalkyl (e.g. $CF_3$), nitro and cyano. There may be from one to three or more substituents which may be the same or different. When R¹ is a substituted phenyl radical the substituents are preferably in the 3, 4 or 5 positions. When a methylenedioxy or ethylenedioxy substituent is present, it is preferably attached to the 3 and 4 positions of the phenyl ring. A halogen substituent (e.g. Cl or Br) may also be present in the 4- or 5-position, or both, in such compounds.

The group $R^2$, when an alkyl group, is preferably one containing from 1 to 4 carbon atoms; it may be linear or branched, viz. methyl, ethyl, n-propyl, iso-propyl, n-butyl, sec-butyl, iso-buty or tert-butyl.

When $R^2$ is an alkenyl group, this may contain from 3 to 5 carbon atoms. Suitable substituents for these alkyl or alkenyl groups include halogen atoms, for example fluorine, chlorine, bromine, and iodine, $C_1$-$C_4$ alkoxy groups for example methoxy, or, in the case where $R^2$ is an alkenyl group, another suitable substituent can be $C_1$-$C_4$ alkyl, for example methyl.

When $R^2$ is an alkynyl group, it may contain from 3 to 5 carbon atoms, for example it may be propargyl. Suitable substituents include chlorine, bromine or iodine, or $C_1$-$C_4$ alkyl, for example methyl.

When $X^1R^2$ is an N-linked 5-membered nitrogen heterocycle it may for example be pyrazole or 1,2,4-triazole, but is preferably pyrazole.

In step (a) of the process as defined above, the halogenating agent employed may be chlorine or bromine, but bromine is preferred. Other halogenating agents can be used in the invention process for example sulphuryl chloride, phosphorus trichloride etc. The halogen should be used in a proportion of one mole for each mole of compound (II), but no excess is necessary. By an inert solvent is meant one which is capable of dissolving both the cyanomethylamide starting material (II) and the halogen but which is not attacked by the halogen. Suitable solvents include esters, such as ethyl acetate, and acetonitrile, but we have found that a particularly suitable solvent is diethylene glycol dimethyl ether ("diglyme"). The solvent should be as free as possible from water. In the case of bromination, with bromine we find that the reaction proceeds more smoothly in the presence of a small proportion of phosphorus tribromide. The halogenation is preferably carried out at a temperature between −10° C. and 50° C., typically in the range of 20° C. to 25° C.

As to the heterocyclic tertiary amine which is added as step (b) to the halogenation mixture during, or after, the halogenation step (a), we find that pyridine is particularly effective, but substituted pyridines, such as the picolines and ethylpyridines, or quinoline and its substituted derivatives, may also be used. As stated above, the heterocyclic tertiary amine is employed in a proportion of from about 1.0 to 2.5 moles, preferably from 1.3 to 2.1 moles (preferably 2 moles) for each mole of halogen reacted; one mole of the amine is used up in forming the quaternary salt (V) whilst the other mole neutralises the hydrogen halide produced in the halogenation reaction. The heterocyclic amine is added to the mixture resulting from step (a) either during, or following completion of, the halogenation reaction without there being any necessity to isolate the intermediate halogenated compound of the formula (VI):

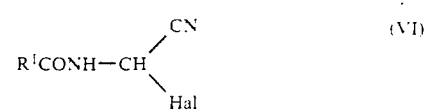

It is indeed preferred not to attempt to isolate it but to proceed direct to step (b). The preferred procedure is to substantially merge steps (a) and (b) but it is preferred to establish the halogenation (e.g., bromination) reaction prior to the addition of the heterocyclic amine (e.g., pyridine). Thus, for example, a lead of about 5 to 25% of the total halogen to be added, e.g., 10%, is established prior to adding the heterocyclic amine substantially simultaneously with the remaining halogen, the molar feed ratio of amine to halogen being preferably between 1.3 and 2.1, and preferably 2. Convenient rates of addition for the bromine and the heterocyclic amine are 0.01 moles per minute and 0.02 moles per minute, respectively. The total addition times for the bromine and the heterocyclic amine, respectively, are the same, for example 100 minutes. Thus when the halogenation is established first, then for the first few minutes, for example the first 10 minutes, the bromine is added alone. Thereafter the heterocyclic amine (for example pyridine) is added concurrently with the bromine, for example for the next 90 minutes. Then the heterocyclic amine is added on its own for the last several, for example, 10 minutes. The quaternary salt (V) is typically a stable substance and it may with advantage be isolated and separated from the accompanying tertiary amine hydrohalide prior to its being treated with the alcohol, thiol or 5-membered nitrogen heterocycle as the case may be. The separation may often be carried out by the simple expedient of washing with water, in which the tertiary amine hydrohalide is soluble but the salt (V) is insoluble.

In the final step (c), the quaternary salt (V) is reacted with the alcohol or thiol or 5-membered nitrogen heterocycle, optionally in a suitable solvent and optionally at a elevated temperature; in the case where the reactant is a lower alkanol, e.g. ethanol, an excess of it may be employed as solvent. When the reaction is complete, the solvent and the liberated tertiary amine may be removed by dissolution into excess water, leaving the insoluble, substantially pure, product (I). Alternatively, the reaction mixture can be drowned into a mixture of brine and a suitable solvent, e.g. ethyl acetate, the solvent layer separated and the product then recovered therefrom by removal of the solvent e.g. by distillation.

The present process is of particular interest for the production of 4-chloro-N-(1-cyano-1-ethoxy)methylbenzamide (VII):

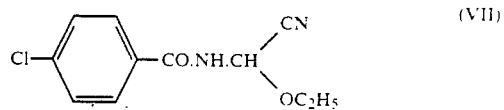

and its 4-bromo analogue, both of which compounds are valuable by reason of their herbicidal and fungicidal properties.

Advantages of the process of the invention over the processes of the prior art are: (i) the rate of addition of the halogen is not critical and there is no need to operate in dilute solution in order to avoid hydration of the cyano group in the starting material (II); (ii) the progress of the halogenation reaction, or the combined, or substantially merged, (a) and (b) reaction, can readily be regulated instead by controlling the temperature of the reaction mixture; the reaction is not particularly exothermic and the temperature can without difficulty be maintained at the preferred levels stated above; (iii) the reaction medium, at the conclusion of step (b), is free from hydrogen halide and may readily be recycled for use in a subsequent batch without further treatment; (iv) the yields of the final product (I) are consistently high. All these advantages are particularly favourable to the large-scale operation of the process in regular manufacture.

The invention is illustrated by the following Example.

EXAMPLE 1

Preparation of
4-chloro-N-(1-cyano-1-ethoxy)methylbenzamide Step
(a) Bromination Diethylene glycol dimethyl ether (1000 ml; water content 0.2%) was charged to a 2-liter, 4-necked flask fitted with stirrer, dropping funnel, thermometer and air condenser.

4-Chloro-N-cyanomethylbenzamide (250 g, 1.285 mole) was added with stirring at ambient temperature and the mixture stirred for 5 minutes to obtain complete dissolution. The resulting solution was cooled to 0°-5° C. in an ice-salt bath, phosphorus tribromide (2 ml) was added, then bromine (205.7 g, 1.285 mole) was added dropwise over a period of 40 minutes whilst maintaining the temperature of the reaction mixture in the range 3°-5° C.

The resulting mixture was stirred for a further 5 minutes, during which time the temperature fell to 2° C.
Step (b): Neutralisation and removal of base hydrobromide.

The bromination mixture from step (a) above was stirred in the ice-salt bath and pyridine (204 g, 2.58 mole) was added dropwise over a period of 20 minutes whilst maintaining the mixture temperature in the range 9°±3° C. The resulting mixture of liquid and yellow solid was stirred for a further 2 hours at 5°-10° C., then filtered so as to remove as much of the diethylene glycol dimethyl ether as possible. The separated solid material was transferred to the original reaction flask and stirred at ambient temperature for 10 minutes with cold water (800 ml). The mixture was then filtered again and washed with cold water (2×75 ml), the washings being rejected and the solid product being pulled as dry as possible. Remaining water was displaced by washing the solid with acetone (5×150 ml) and finally the product was dried in vacuo at 45° C. The yield of pyridinium salt was 228 g.
Step (c): Ethoxylation Absolute ethanol (300 ml) was charged to a 1-liter 4-necked flask fitted with a stirrer, thermometer and reflux condenser and the dried pyridinium salt from step (b) (228 g) was added with stirring at ambient temperature. The mixture was then heated to reflux temperature and stirred under reflux until complete dissolution of the salt had occurred, then for 5 minutes more. A mixture of cold water (150 ml) and a 10% solution of a dispersing agent, for example a polyglyceryl ricinoleate such as that commercially available under the Trade Mark "DISPERSOL OG," (10 ml) was stirred rapidly whilst the above ethanol solution was added to it in a thin stream over a period of 15 minutes.

After a further 30 minutes stirring, the precipitated title compound was separated by filtration; washed with excess water, pulled as dry as possible and then dried to constant weight in vacuo at 50° C. The yield of product was 159 g.

EXAMPLE 2

This Example shows the preparation of the same compound as that described in Example 1, but it illustrates an alternative procedure for isolating the product.

The product of Example 1, steps (a) and (b), was repeated, using the following amounts of materials:
Diethylene glycol dimethyl ether 6000 ml
4-Chloro-N-cyanomethylbenzamide 1167 g
Phosphorus tribromide a few drops
Bromine 306 ml
Pyridine 972 ml The mustard-coloured pyridinium salt obtained in step (b) was treated with absolute ethanol (2000 ml), stirred under nitrogen to give a yellow suspension which changed to a red solution on heating to reflux temperature. Once complete solution had been achieved, the mixture was allowed to cool for 30 minutes. Saturated brine (4400 ml) and ethyl acetate (6600 ml) were added, the mixture stirred and then left to separate into two dark-coloured layers. The organic layer was separated, washed with brine (2×2300 ml) to remove the ethanol, then dried (anhydrous MgSO₄), filtered and concentrated, giving a brown solid (963 g, 67% crude yield). This product was recrystallised from carbon tetrachloride (2.5 ml per g) to give a beige solid of mp. 102°-106° C. (618 g, 43% yield). A further recrystallisation gave material of mp. 112°-114° C. which was shown to be homogenous by thin layer chromatography and was identified by IR analysis as being the title compound. A further quantity of the compound was removed from the first recrystallisation as a second crop.

EXAMPLE 3

This Example illustrates the preparation of the pyridine quaternary salt by a modified method involving the co-addition of bromine and pyridine. The reaction sequence is as follows:

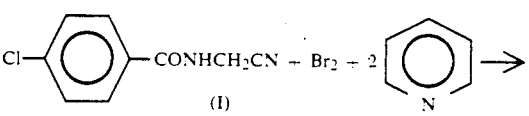

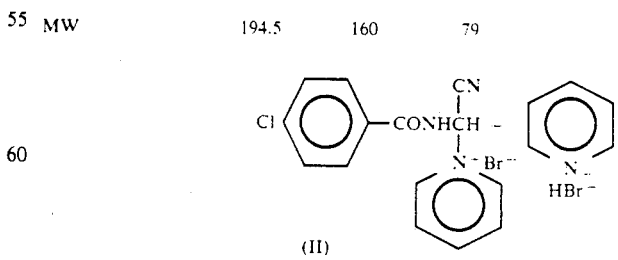

The following substances were used in the reaction in the amounts shown:

|  | Weight (g) | Moles |
| --- | --- | --- |
| N-cyanomethyl-4-chlorobenzamide (I) | 194.5 | 1.0 |
| Bromine | 160 | 1.0 |
| Pyridine | 158 | 2.0 |
| Phosphorus tribromide | 2 |  |
| Diglyme | 700 |  |

The N-cyanomethyl-4-chlorobenzamide (I) was dissolved in the diglyme at 20°–25° C. and phosphorus tribromide was added.

The bromine was added at a rate of 0.01 moles/min. The total addition time for the bromine was 100 minutes. Pyridine was added at a rate of 0.02 moles/min. The total addition time for the pyridine was 100 minutes. During the co-addition of reactants the reaction mixture temperature was maintained between 20°–25° C. using an external ice/water bath and 10% of the bromine was added before the addition of the pyridine commenced. The precipitated solid was filtered, washed with acetone, and dried to yield 467.7 g product.

The co-produced pyridinium bromide was washed out with water and the remaining pyridine quaternary salt (II) was filtered, washed with acetone, and dried, to give 303 g of pyridine quaternary salt.

EXAMPLE 4

This Example illustrates the preparation of the pyridine quaternary salt using pyridinium hydrobromide perbromide as brominating agent. The reaction sequence is as follows:

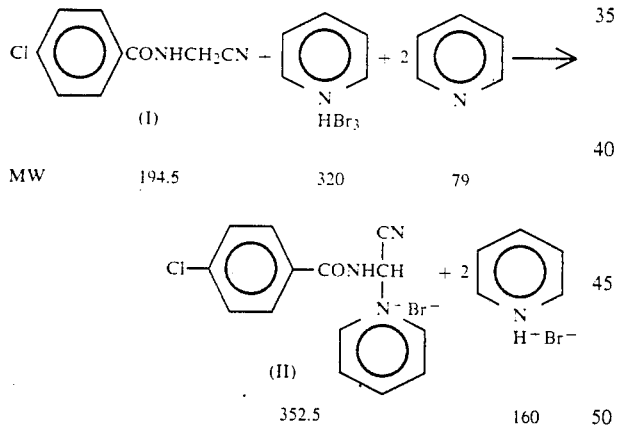

MW    194.5        320        79

352.5                160

METHOD (a) Bromination Stage

N-cyanomethyl-4-chlorbenzamide (I) (9.7 g, 0.05 mole) was dissolved in diglyme (35 g) at 20° C. Pyridinium hydrobromide perbromide (16.0 g, 0.05 mole) was added over about five minutes maintaining the reaction temperature at about 20° C. using an ice/water bath.

(b) Quaternisation Stage

Pyridine (7.9 g, 0.10 mole) was added to the foregoing over about five minutes maintaining the reaction temperature between 20°–25° C. using an ice/water bath.

The precipitated solid was filtered, washed with water to remove the co-produced pyridinium bromide, washed with acetone, and then dried to give 13.3 g of the pyridine quaternary salt of formula (II).

EXAMPLE 5

This Example illustrates the preparation of the pyridine quaternary salt using a mixture of bromine and pyridine perbromide as brominating agent.

The reaction sequence is as follows:

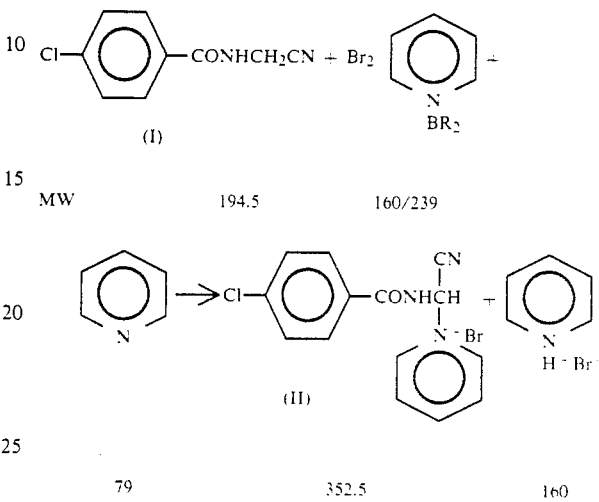

MW    194.5    160/239

352.5            160

METHOD (a) Bromination Stage

N-cyanomethyl-4-chlorobenzamide (I) (9.7 g, 0.05 mole) was dissolved in diglyme (35 g) at 20° C. PBr₃ (0.1 g) and bromine (1.0 g, 0.006 mole) were added to initiate the bromination reaction followed by pyridine perbromide (10.5 g, 0.044 mole) over about five minutes maintaining the reaction temperature at about 20° C. using an ice/water bath.

(b) Quaternisation Stage

Pyridine (3.95 g, 0.05 mole) was added to the foregoing over about five minutes maintaining the reaction temperature between 20°–25° C. using an ice/water bath.

The precipitated solid was filtered, washed with water to wash out the co-produced pyridinium bromide, washed with acetone, and then dried to give 14.3 g, of the pyridine quaternary salt of formula (II).

We claim:

1. A process for the production of a substituted amide derivative of the formula (I):

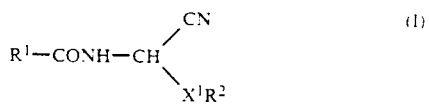

in which $R^1$ is phenyl or naphthyl optionally substituted with one or more of fluorine, chlorine, bromine, iodine, $C_1$–$C_4$ alkoxy, methylenedioxy and ethylenedioxy, $C_1$–$C_4$ alkyl, $C_1$–$C_4$ alkylthio, $C_1$–$C_4$ haloalkyl, nitro and cyano; $R^2$ is an alkyl group containing from 1 to 4 carbon atoms or an alkenyl group or alkynyl group, each containing from 3 to 5 carbon atoms, such alkyl, alkenyl or alkynyl group being optionally substituted with one or more halogen atoms, $C_1$–$C_4$ alkoxy groups or, in the case where $R^2$ is an alkenyl or alkynyl group, a $C_1$–$C_4$ alkyl group, $X^1$ is —O— or —S—; or $X^1R^2$ together represent an N- linked 5-membered nitrogen heterocycle which is a pyrazole, or 1,2,4-triazole group, the process comprising the steps of (a) treatment with a halogenating agent selected from the group consisting of chlorine and bromine in an inert solvent of an N-cyanomethylamide of the formula (II):

$$R^1-CONH-CH_2CN \qquad (II)$$

(b) after a period of several minutes commencing the addition of pyridine concurrently with the addition of halogenating agent in the proportion of from 1.3 to 2.1 moles of pyridine for each mole of halogenating agent to form a quaternary salt of the formula (V):

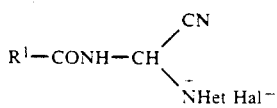

where Hal represents chlorine or bromine and Het represents the pyridine residue;

(c) continuing to add pyridine for several minutes after halogen addition is terminated; and (d) treating the salt (V) with a reagent of the formula $R^2X^1H$ to obtain (I).

2. A process as claimed in claim 1 wherein the halogen is used in a proportion of 1 mole for each mole of compound (II) and the heterocyclic in a proportion of 2 moles for each mole of halogen.

3. A process as claimed in claim 1 wherein the inert solvent is ethyl acetate, acetonitrile or diethylene glycol dimethyl ether.

4. A process as claimed in claim 1 wherein the halogen employed in step (a) is bromine and a small amount of phosphorus tribromide is present.

5. A process as claimed in claim 1 wherein step (c) is effected using the isolated and separated salt V and conducting the reaction with the reagent $R^2X^1H$ in a solvent.

6. The process of claim 1 wherein the substituted amide is 4-chloro-N-(1-cyano-1-ethoxy)methyl-benzamide.

7. The process of claim 1 wherein the substituted amide is 4-bromo-N-(1-cyano-1-ethoxy)methyl-benzamide.

* * * * *